United States Patent [19]
Jenkins et al.

[11] Patent Number: 5,891,444
[45] Date of Patent: *Apr. 6, 1999

[54] HIV-1 PROPHYLACTIC COMPOSITION AND METHOD

[75] Inventors: Sharon Jenkins, Peabody; Yichen Lu, Wellesley; Lendon Payne, Arlington; Bryan Roberts, Cambridge, all of Mass.

[73] Assignee: Virus Research Institute, Inc., Cambridge, Mass.

[ * ] Notice: The term of this patent shall not extend beyond the expiration date of Pat. No. 5,494,673.

[21] Appl. No.: 474,446

[22] Filed: Jun. 7, 1995

[51] Int. Cl.$^6$ .......................... A61K 39/21; A61K 51/00; A61K 39/42; A61K 39/385

[52] U.S. Cl. .................. 424/208.1; 424/1.61; 424/280.1; 424/160.1; 424/193.1

[58] Field of Search ............................... 424/1.61, 208.1, 424/280.1, 160.1, 193.1

[56] References Cited

U.S. PATENT DOCUMENTS 5,494,673   2/1996   Andrianov et al. .................. 424/280.1

OTHER PUBLICATIONS

Fahey et al., Status of immune-based therapies in HIV infection and AIDS, Clin. exp. Immunol. 88, 1–5, see entire document, 1992.

Fox, No winners against AIDS, Bio/Technology, vol. 12, p. 128, 1994.

Cohen et al., Ionically Cross-Linkable Polyphosphazene: A Novel Polymer for Microencapsulation, J. Am. Chem. Soc., 112, 7832–7833, see p. 7833, column 1, paragraph 1, 1990.

Sodroski et al., Molecular analysis of single cell lysis by HIV-1, Int. Conf. AIDS (Canada), Jun. 4–9, 5 p. 513, see Abstract, 1989.

*Primary Examiner*—Donald E. Adams
*Assistant Examiner*—Hankyel T. Park
*Attorney, Agent, or Firm*—Raina Semionow

[57] ABSTRACT

A composition and method for inducing a protective immune response to HIV-1 in an individual, of (a) a replication incompetent HIV-1, HIV-1 pseudovirus, HIV-1 VLP or oligomeric gp120; and (b) a water soluble polyphosphazene polyelectrolyte, wherein (a) and (b) are present in an amount effective to induce a protective immune response against HIV-1.

4 Claims, 7 Drawing Sheets

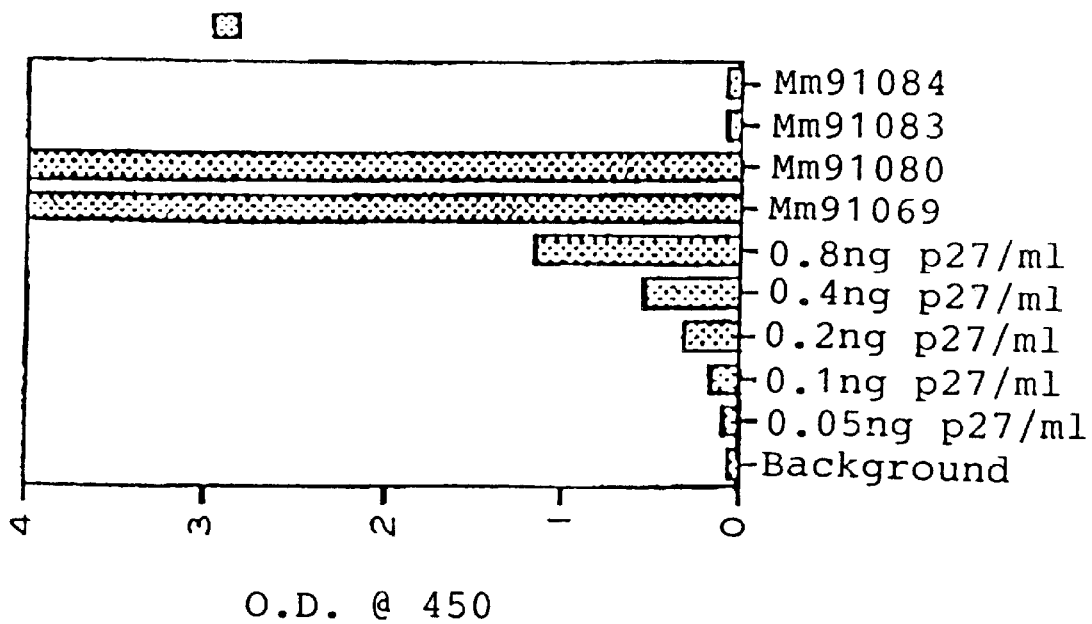
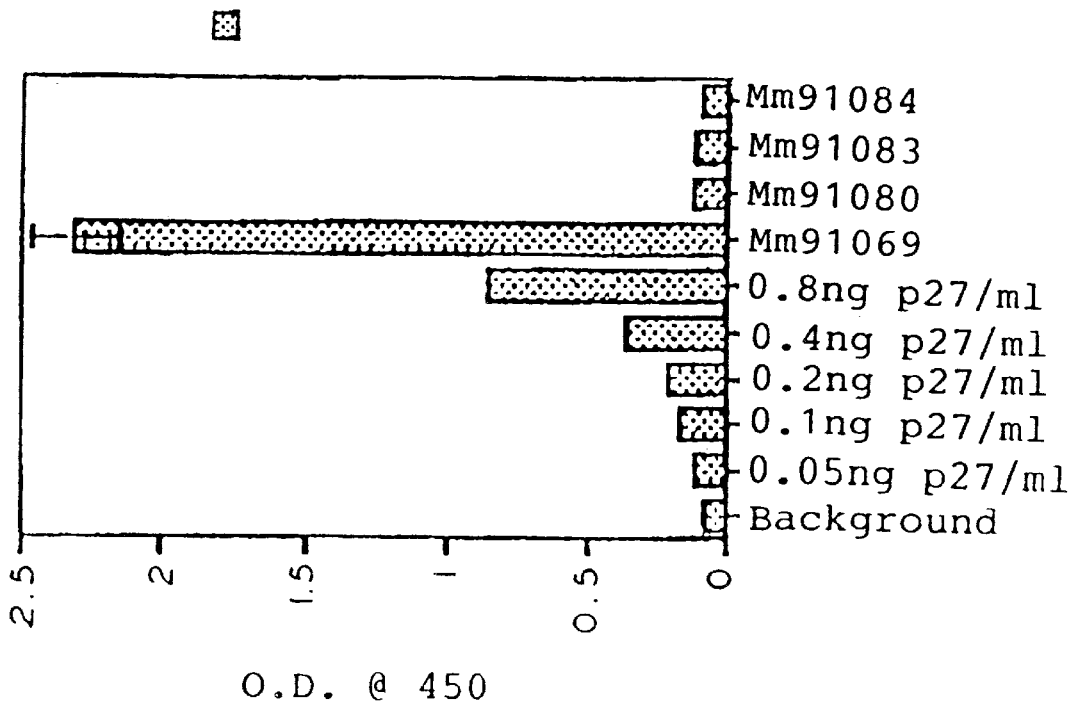

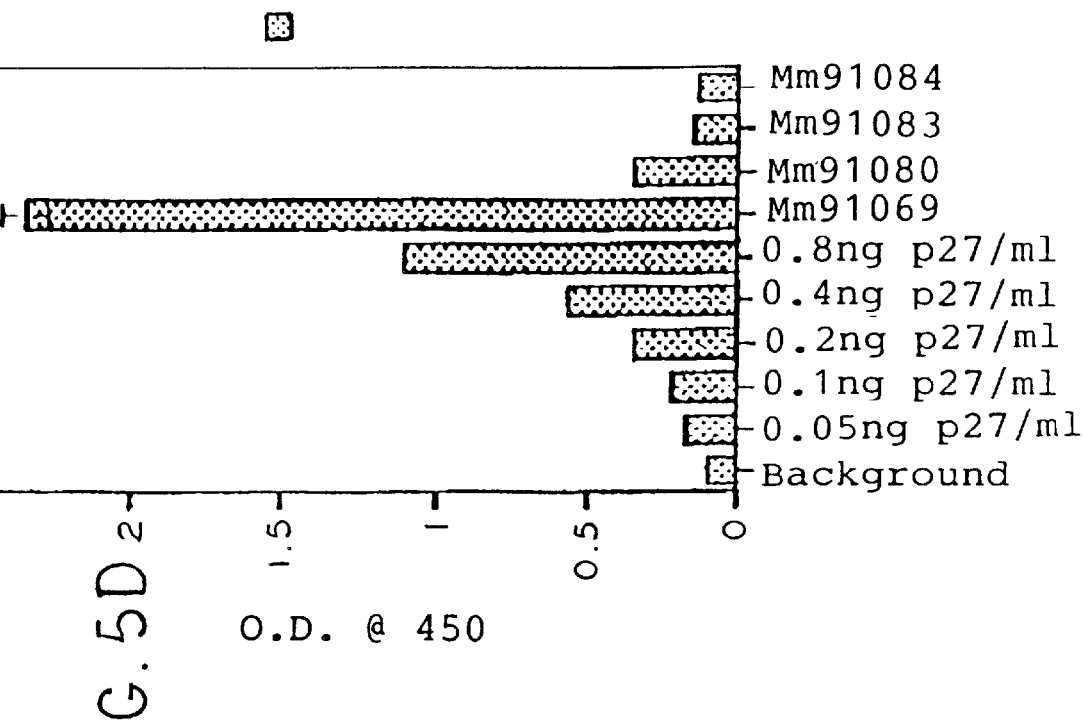
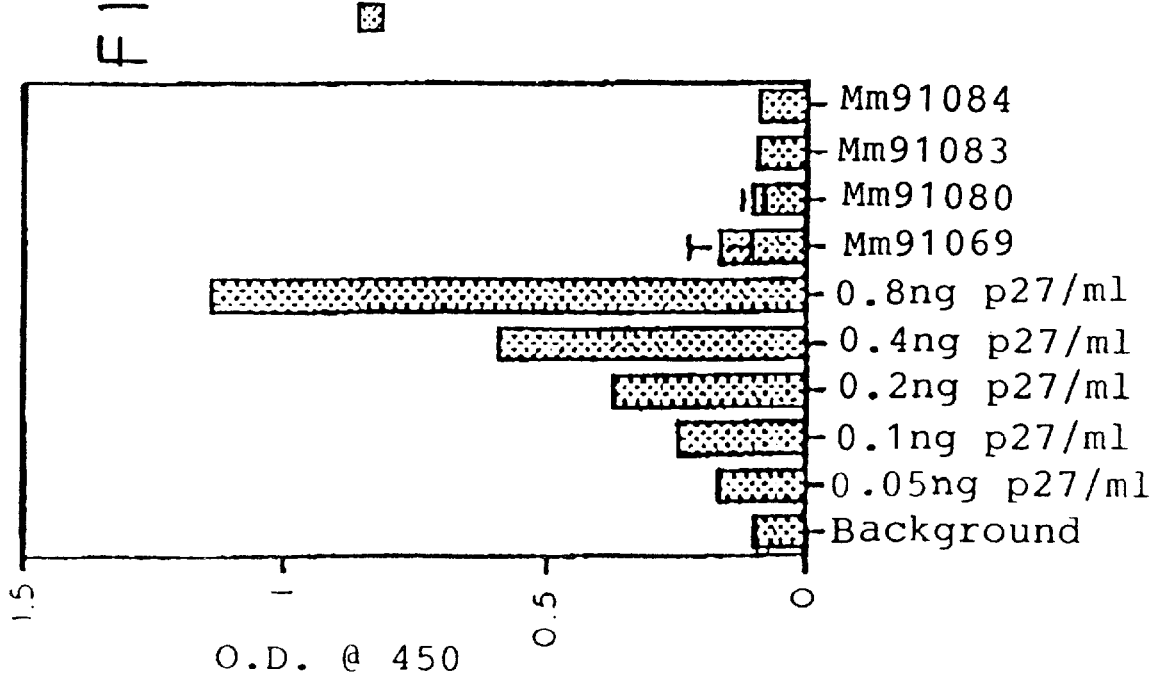
FIG. 5C
FIG. 5D

HIV-1 PROPHYLACTIC COMPOSITION AND METHOD

One of the obstacles to HIV-1 vaccine development has been the lack of an applicable animal model. The only non-human host in which HIV-1 can efficiently replicate is the chimpanzee. However, the cost and availability of this endangered species makes it almost impossible to do sufficient experimentation to test vaccine efficacy. Although SIV-1 causes an AIDS-like disease in monkeys and its genetic organization shares remarkable similarity with HIV-1, prophylactic studies illustrate that the immuno reactive epitopes of the SIV envelope glycoprotein are different from its HIV counterpart. This critical difference in the major protective antigen invalidated the use of SIV as a predictive model for HIV prophylactic reagents (Weiss et al, Nature, 324:572–5, 1986).

In the past ten years, several HIV-1 vaccine candidates have been tested in chimpanzees. Some have produced promising results. From vaccine development point of view, further studies should test the optimal vaccine formulation, including the comparison of different adjuvants, the dose of antigens and the optimal schedule of immunization that will stimulate the maximal protection against different strains of virus challenge. It is, however, impossible to conduct these necessary studies in a significant number of chimpanzees. According to a report from the AIDS Vaccine Surveillance System (AVSS), the total number of chimpanzees used in HIV-1 vaccine challenge studies as of 1992 was 32. These studies include at least five different type of antigens, fourteen different protocols, and a number of adjuvants.

SUMMARY OF THE INVENTION

In one aspect the invention provides a composition for inducing a protective immune response to HIV-1 in an individual which comprises (a) a member selected from the group consisting of replication incompetent HIV-1, HIV-1 pseudovirus, HIV-1 VLP and oligomeric gp120 and (b) a water soluble polyphosphazene polyelectrolyte, wherein (a) and (b) are present in an amount that induces a protective immune response against HIV-1.

In another aspect the invention provides a method for inducing a protective immune response to HIV-1 in an individual which comprises administering to said individual an amount that induces a protective immune response against HIV-1 of a composition that comprises (a) a member selected from the group consisting of replication incompetent HIV-1, HIV-1 pseudovirus, HIV-1 VLP and oligomeric gp120 and (b) a water soluble polyphosphazene polyelectrolyte.

In another aspect of the invention provides a SHIV construct comprising an SIV-1 virus (1) in which at least one simian envelope gene has been replaced by its corresponding HIV-1 gene; (2) which is capable of replicating in macaque monkeys and (3) which expresses the HIV-1 vpu gene that is absent in SIV genomes.

In another aspect the invention demonstrates the utility of SHIV chimeric viruses in a macaque monkey, rather than a chimpanzee, animal model in efficacy studies of HIV prophylactics.

BRIEF DESCRIPTION OF THE DRAWINGS

The invention will now be further described by reference to a brief description of each of the Figures, but in no way are they a limitation of the scope of the invention.

FIG. 5 shows the results of analysis for SHIV replication by peripheral blood co-culture with human T cells.

DETAILED DESCRIPTION OF THE INVENTION

Figure 1:
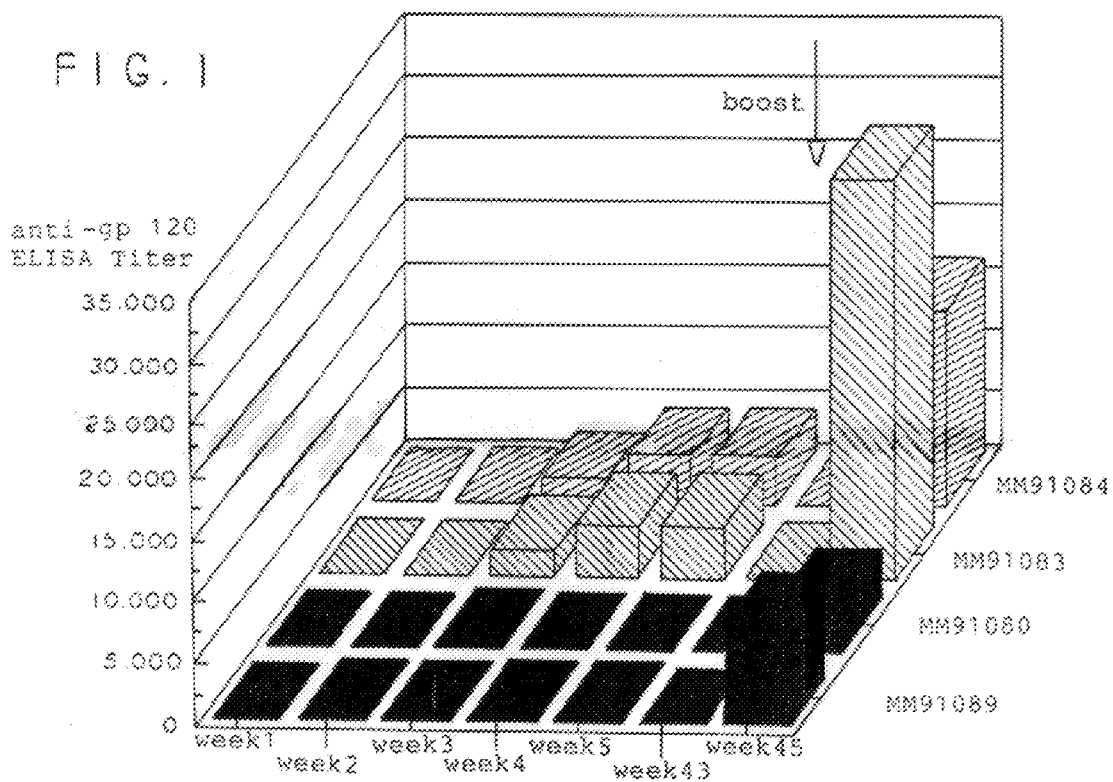
FIG. 1 graphically illustrates that all four (4) of the macaques inoculated with HIV-1 virus as described in Example 1 had detectable serum antibodies against HIV-1 gp120 by week 5 after the first inoculation and that by week 43 the antibody level had fallen below the level of detection.

The invention will now be described in more detail with respect to numerous embodiments and examples in support thereof.

In the retrovirus, of which HIV-1 is an example of particular importance, genome there are non-coding sequences known as long terminal repeat (LTR) sequences at each end, a packaging sequence designated by the Greek letter psi ($\psi$) that is required for "packaging" retroviral RNA into mature-virus particles, the gag (group associated antigen) gene, the pol gene and the env gene. The gag gene encodes a "polyprotein" that is proteolytically cleaved into three or four proteins that make up the core protein or capped of the virus particle structure. The pol gene encodes a "polyprotein" that is cleaved to provide reverse transcriptase and integrase, needed for "integrating" or inserting the viral genetic material into the host cell chromosome as double-stranded DNA. The env gene encodes another polyprotein which is cleaved to form those proteins (gp160, which is cleaved to form gp120 and gp40) which make the "coat" or "envelope" of the virus. The enzyme responsible for all of these cleavages is one of the proteins coded for by the pol gene. The LTR sequences are necessary for integration and for the initiation and regulation of transcription (i.e., they are essentially retroviral "promoters").

The HIV-1 virus has several small genes, in addition to the standard retroviral genome, with various regulatory functions. One of these, the nef gene, is adjacent the 3' LTR thus, through various alternative splicing configurations expression of this gene or another detectable gene, such as an antibiotic resistance or other marker gene, under control of a transcriptional initiation sequence at the 5' end of the genome demonstrates active transcription is occurring at the coding regions between them.

As noted above, the present invention provides a vaccine composition. The first component of the vaccine composition constitutes certain select HIV preparations, particularly replication incompetent or inactivated whole HIV, an HIV-1 pseudovirus, a "virus-like particle" (VLP) vector or an oligomerized gp120 HIV-1 protein.

The whole HIV-1 can be inactivated by any of the techniques known for inactivating viruses, such as heat or formalin inactivation. A suitable method of inactivation is illustrated in the working examples herein.

The term "HIV-1 pseudovirus" refers to HIV-1 protein constructs that have essentially the same antigenic profile as the whole HIV-1 virus, but no genome. By conventional recombinant cloning techniques, the 5' LTR of the HIV-1 is replaced with a strong heterologous promoter, the ψ packaging signal is removed, the HIV-1 specific nef gene, which is just upstream of the 3' LTR end of the genome, is replaced with a selectable marker and the 3' LTR is replaced with a polyadeylation signal. A suitable cell line is transfected with this construct and colonies which express the marker are selected. Since the marker is near the 3' end of the coding region, its expression, resulting from alternative splicing of the RNA, is evidence of the expression of all of the other HIV-1 proteins between it and the strong promoter at the 5' end. Production of the intact proteinn prtion of the particle is demonstrated by election microscopy and immunoprecipitation of the particle with HIV-1 antiserum. Since both the LTRs are absent, the risk of homologous recombination is avoided. Since the ψ packaging signal is absent, the HIV-1 RNA cannot be packaged into the particle. The resulting "pseudovirus" has an authentic HIV-1 coat or envelope and an authentic HIV-1 capsid, but no genetic material. Since its protein structure is that of HIV-1 it is an ideal antigen for inducing a protective immunity to HIV-1 and is safe because the machinery for creating complete HIV-1 virus is absent.

The terms "virus-like particle" or "VLP" refer to a retroviral vector containing a promoter and only the gag55 and env genes of HIV-1. Under electron microscopy it appears as an HIV-1 envelope with no genomic or core structure components. It is produced by a non-HIV virus or expression vector into which the HIV-1 gag55 and env genes have been introduced and from which they are expressed.

The term "oligomerized gp120" refers to a chain or complex of gp120 protein nonomeric units, preferably a tetramer. This oligomerized gp120 is insoluble, unlike the monomeric gp120, and is believed to be the or a principal source of antigenicity, when in a insoluble form, by which the inactivated whole HIV-1, HIV-1 pseudovirus and viruslike particle induce the protective immune response to HIV-1 in vaccine recipients.

The second component of the vaccine composition of the invention is a water soluble polyphosphazine polyelectrolyte immunoadjuvant. In a preferred embodiment, the phosphazene is a polyelectrolyte that is biodegradable and that exhibits minimal toxicity when administered to animals, particularly including humans.

In one embodiment, the polymeric adjuvant is an poly (organophosphazene) with (i) ionized or ionizable pendant groups that contain, for example, aryl carboxylic acid ethers and amines, or hydroxyl moieties, and (ii) pendant groups that are susceptible to hydrolysis under the conditions of use, to impart biodegradability to the polymer. Suitable hydrolyzable groups include, for example, chlorine, amino acid, amino acid ester, imidazole, glycerol, and glucosyl. When cross-linked with a multivalent ion, the polymer becomes less soluble, resulting in slower release of the polymer from the site of administration.

The term "alkyl" refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term "(alkyl or dialkyl) amino" refers to an amino group that has one or two alkyl substituents, respectively.

The terms "alkenyl" and "alkynyl" refer to a C2 to C20 straight or branched hydrocarbon with at least one double or triple bond, respectively.

The term "aryl" refers to phenyl or substituted phenyl, wherein the substituent is halo, alkyl, alkoxy, alkylthio, haloalkyl, hydroxyalkyl, alkoxyalkyl, methylenedioxy, cyano, C(O) (lower alkyl), —$CO_2H$, —$SO_3H$, —$PO_3H$, —$CO_2$alkyl, amide, amino, alkylamino and dialkylamino, and wherein the aryl group can have up to 3 substituents.

The term "aliphatic" refers to hydrocarbon, typically of $C_1$ to $C_{20}$, that can contain one or a combination of alkyl, alkenyl, or alkynyl moieties, and which can be straight, branched, or cyclic, or a combination thereof.

The term "halo" includes fluoro, chloro, bromo, and iodo.

The term "aralkyl" refers to an aryl group with an alkyl substituent.

The term "alkaryl" refers to an alkyl group that has an aryl substituent, including benzyl, substituted benzyl, phenethyl or substituted phenethyl, wherein the substituents are as defined above for aryl groups.

The terms "heteroaryl" or "heteroaromatic" refer to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term "pharmaceutically acceptable cation" refers to an organic or inorganic moiety that carries a positive charge and that can be administered as a countercation in a phosphazene polyelectrolyte.

The term "heteroalkyl" refers to a alkyl group that includes a heteroatom such as oxygen, sulfur, or nitrogen (with valence completed by hydrogen or oxygen) in the carbon chain or terminating the carbon chain.

Polyphosphazenes are polymers with backbones consisting of alternating phosphorus and nitrogen, separated by alternating single and double bonds. Each phosphorous atom is covalently bonded to two pendant groups ("R"). The repeat unit in the polyphosphazenes of this invention has the following formula:

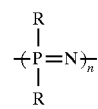

wherein each R is independently selected from the group consisting of aliphatic, aryl, aralkyl, alkaryl, carboxylic acid, heteroaromatic, carbohydrates, including glucose, heteroalkyl, halogen, (aliphatic) amino- including alkylamino-, heteroaralkyl, di(aliphatic) amino- including dialkylamino-, arylamino-, diarylamino-, alkylarylamino-, -oxyaryl including but not limited to -oxyphenylCO$_2$H, -oxyphenylSo$_3$H, -oxyphenylhydroxyl and -oxyphenylPO$_3$H; -oxyaliphatic including -oxyalkyl, -oxy (aliphatic)CO$_2$H, -oxy-aliphatic)SO$_3$H, -oxy-aliphatic) PO$_3$H, and -oxy(aliphatic)hydroxyl, including -oxy(alkyl) hydroxyl; -oxyalkaryl, -oxyaralkyl, -thioaryl, -thioaliphatic including -thioalkyl, -thioalkaryl, -thioaralkyl, —NHC(O) O—(aryl or aliphatic), —O—[(CH$_2$)$_x$O]$_y$NH$_2$, —O—[ (CH$_2$)$_x$O]$_y$CH$_2$)$_x$NH (CH2)$_x$SO$_3$H, and —O—[(CH$_2$)$_x$O] y—(aryl or aliphatic), wherein x is 1–8 and 6 is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

In one embodiment, the immunoadjuvant is a biodegradable polyphosphazene of the formula:

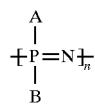

wherein A and B can vary independently in the polymer, and can be:
  (i) a group that is susceptible to hydrolysis under the conditions of use, including but not limited to chlorine, amino acid, amino acid ester (bound through the amino group), imidazole, glycerol, or glucosyl; or
  (ii) a group that is not susceptible to hydrolysis under the conditions of use, including, but not limited to an aliphatic, aryl, aralkyl, alkaryl, carboxylic acid, heteroaromatic, heteroalkyl, (aliphatic)amino- including alkylamino-, heteroaralkyl, di(aliphatic) aminoincluding dialkylamino-, arylamino-, diarylamino-, alkylarylamino-, -oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic) CO$_2$H, -oxy(aliphatic)SO$_3$H, -oxy(aliphatic)PO$_3$H, and -oxy(aliphatic)hydroxyl, including -oxy(alkyl) hydroxyl; -oxyalkaryl, -oxyaralkyl, -thioaryl, -thioaliphatic including -thioalkyl, -thioalkaryl, or thioaralkyl;
  wherein the polymer contains at least one percent or more, preferably 10 percent or more, and more preferably 80 to 90 percent or more, but less than 100% of repeating units that are not susceptible to hydrolysis under the conditions of use, and
  wherein n is an integer of 4 or more, and preferably between 10 and 20,000 to 300,000.

It should be understood that certain groups, such as heteroaromatic groups other than imidazole, hydrolyze at an extremely slow rate under neutral aqueous conditions, such as that found in blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select that polyphosphazene that provides the desired biodegradation profile for the targeted use.

The degree of hydrolytic degradability of the polymer will be a function of the percentage of pendant groups susceptible to hydrolysis and the rate of hydrolysis of the hydrolyzable groups. The hydrolyzable groups are replaced by hydroxyl groups in aqueous environments to provide P—OH bonds that impart hydrolytic instability to the polymer.

In other embodiments, the immunoadjuvant is: (i) a nonbiodegradable polyphosphazene wherein none, or virtually none, of the pendant groups in the polymer are susceptible to hydrolysis under the conditions of use, or (ii) a completely biodegradable polyphosphazene wherein all of the groups are susceptible to hydrolysis under the conditions of use (for example, poly[di(glycinato)phosphazene]).

The phosphazene polyelectrolytes herein contain ionized or ionizable pendant groups that render the polyphosphazene anionic, cationic or amphophilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte immunoadjuvant contains pendant groups that include carboxylic acid, sulfonic acid, or hydroxyl moieties. While the acidic groups are usually on nonhydrolyzable pendant groups, they can alternatively, or in combination, also be positioned on hydrolyzable groups. An example of a phosphazene polyelectrolyte having carboxylic acid groups as side chains is shown in the following formula:

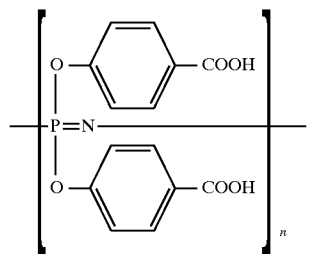

wherein n is an integer, preferably an integer between 10 and 10,000 to 300,000. This polymer has the chemical name poly[di(carboxylatophenoxy)phosphazene] or, alternatively, poly[bis(carboxylatophenoxy)phosphazene] (PCPP).

The phosphazene polyelectrolyte is preferably biodegradable to prevent eventual deposition and accumulation of polymer molecules at distant sites in the body, such as the spleen. The term biodegradable, as used herein, means a polymer that degrades within a period that is acceptable in the desired application, typically less than about five years and most preferably less than about one year, once exposed to a physiological solution of pH 6–8 at a temperature of approximately 25° C.–37° C.

Most preferably the polymer is a poly (organophosphazene) that includes pendant groups that include carboxylic acid moieties that do not hydrolyze under the conditions of use and pendant groups that are susceptible to hydrolysis under the conditions of use. Examples of preferred phosphazene polyelectrolytes with hydrolysis-sensitive groups are poly[di(carboxylatophenoxy) phosphazene-co-di(amino acid)phosphazene-co-(carboxylatophenoxy) (amino acid)phosphazene], specifically including poly[di(carboxylatophenoxy) phosphazene-co-di(glycinato)phosp hazene-co-(carboxylatophenoxy)(glycinato)phosphazene], and poly [di (carboxylatophenoxy) phosphazene-co-di (chloro) phosphazene-co-(carboxylatophenoxy) (chloro) phosphazene].

The toxicity of the polyphosphazene was determined using cell culture experiments well known to those skilled in the art. For example, toxicity of poly[di (carboxylatophenoxy) phosphazene] was determined in cell culture by coating cell culture dishes with the poly[di (carboxylatophenoxy) phosphazene]. Chicken embryo fibroblasts were then seeded onto the coated petri dishes. Three days after seeding the chicken embryo fibroblasts, the cells had become flattened and spindles formed. Under phase contrast microscopy, mitotic figures were observed. These observations provide evidence of the non-toxicity of poly[di(carboxylatophenoxy)phosphazene] to replicating cells.

Crosslinked polyphosphazenes for use as immunoadjuvants can be prepared by combining a phosphazene polyelectrolyte with a metal multivalent cation s~uch as zinc, calcium, bismuth, barium, magnesium, aluminum, copper, cobalt, nickel, or cadmium.

Polyphosphazenes, including phosphazene polyelectrolytes, can be prepared by a macromolecular nucleophilic substitution reaction of poly(dichloro phosphazene) with a wide range of chemical reagents or mixture of reagents in accordance with methods known to those skilled in the art. Preferably, the phosphazene polyelectrolytes are made by reacting the poly(dichloro phosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly (dichlorophosphazene) and the reaction conditions as necessary. Preferred polyphosphazenes for immunoadjuvant activity have a molecular weight of over 1,000.

For example, poly[(carboxylatophenoxy)(glycinato) phosphazene] (PC-GlPP) is prepared by the nucleophilic substitution reaction of the chlorine atoms of the poly (dichlorophosphazene) with propyl phydroxybenzoate and ethyl glycinate hydrochloride (PC-GlPP synthesis). The poly[(aryloxy) (glycinato)phosphazene] ester thus obtained is then hydrolyzed to the corresponding poly(carboxylic acid). Other polyphosphazenes can be prepared as described by Allcock, H. R.; et al., Inorg. Chem. 11, 2584 (1972); Allcock, H. R.; et al., Macromolecules 16, 715 (1983); Allcock, H. R.; et al., Macromolecules 19,1508 (1986); Allcock, H. R.; et al., Biomaterials 19, 500 (1988); Allcock, H. R.; et al., Macromolecules 21, 1980 (1988); Allcock, H. R.; et al., Inorg. Chem. 21(2), 515521 (1982); Allcock, H. R.; et al., Macromolecules 22:7579 (1989); U.S. Pat. Nos. 4,440,921, 4,495,174, 4,880,622 to Allcock, H. R.; et al.; U.S. Pat. No. 4,946,938 to Magill, et al., U.S. Pat. No. 5,149,543 to Cohen et al., and the publication of Grolleman, et al., J. Controlled Release 3,143 (1986), the teachings of which, and polymers disclosed therein, are incorporated by reference herein.

An immunogenic composition, or vaccine, is prepared by combining the polymer adjuvant with an antigen. Approximately 0.5–0.0001 parts of antigen is added to one part polymer, preferably by stirring a solution of polymer and antigen until a solution or suspension is obtained, preferably for 10 minutes or more at 25° C. The polymer is preferably combined with the antigen using a method dispersing the antigen uniformly throughout the adjuvant. Methods for liquifying the polymer include dissolving the polymer in an aqueous-based solvent, preferably having a pH range of between 7.1 and 7.7, and melting the polymer. The latter is useful only when the antigen is stable at the polymer melting temperature. The antigen is then mixed with the polymer. The polymer and the antigen, in solid form, for example, when the antigen is lyophilized, can also be physically mixed together, for example, by compression molding. The polymer can also be used to encapsulate the antigen, for example, using the method of U.S. Pat. No. 5,149,543 to Cohen et al., the teachings of which are incorporate herein, or by spray drying a solution of polymer and antigen. Alternatively, microspheres containing the antigen and adjuvant can be prepared by simply mixing the components in an aqueous solution, and then coagulating the polymer together with the substance by mechanical forces to form a microparticle. The microparticle can be stabilized, if necessary or desired, using electrolytes, pH changes, organic solvents, heat or frost to form polymer matrices encapsulating biological material.

In a preferred embodiment, approximately one part of polymer is dissolved in 10 parts 3% $Na_2CO_3$ aqueous solution while stirring, then 10 to 90 parts phosphate buffer pH 7.4 is slowly added.

Polymer-Antigen Conjugates

The polymer can also be covalently conjugated with the antigen to create a water-soluble conjugate in accordance with methods well-known to those skilled in the art, usually by covalent linkage between an amino or carboxyl group on the antigen and one of the ionizable side groups on the polymer.

In an alternative preferred embodiment, the polymer is cross-linked with a multivalent ion, preferably using an aqueous solution containing multivalent ions of the opposite charge to those of the charged side groups of the polyphosphazene, such as multivalent cations if the polymer has acidic side groups or multivalent anions if the polymer has basic side groups.

Preferably, the polymers are cross-linked by di and trivalent metal ions such as calcium, copper, aluminum, magnesium, strontium, barium, tin, zinc, and iron, organic cations such as poly(amino acid)s, or other polymers such as poly(ethyleneimine), poly(vinylamine) and polysaccharides.

Additives to the polymer-adjuvant mixture

It will be understood by those skilled in the art that the immunogenic vaccine composition can contain other physiologically acceptable ingredients such as water, saline or a mineral oil such as DrakeolTM, MarkolTM, and squalene, to form an emulsion.

The immunogenic composition can be administered as a vaccine by any method known to those skilled in the art that elicits an immune response, including parenterally, orally, or by transmembrane or transmucosal administration. Preferably, the vaccine is administered parenterally (intravenously, intramuscularly, subcutaneously, intraperitoneally, etc.), and preferably subcutaneously. Non-limiting examples of routes of delivery to mucosal surfaces are intranasal (or generally, the nasal associated lymphoid tissue), respiratory, vaginal, and rectal.

The dosage is determined by the antigen loading and by standard techniques for determining dosage and schedules for administration for each antigen, based on titer of antibody elicited by the polymer-antigen administration, as demonstrated by the following examples.

Although in the preferred embodiment the polymer antigen mixture is administered simultaneously, in an alternative embodiment, the polymer and antigen are administered separately to the same or nearby site. The polymer serves to attract cells of the immune system to the site, where they process the antigen.

The various aspects and embodiments of the invention will be further understood by reference to the following non-limiting examples.

EXAMPLE 1

The Preparation of Whole Inactivated HIV-1 Virus

A HIV-1 virus producer cell line was established from HIV-1 infected human T cells. The cells were cultured in RPMI medium with 10% FCS plus antibiotics at a density of $10^6$ cells per ml. After three days in culture, the supernatant was collected by low speed centrifugation at 3000 rpm/min for 10 minutes. The viruses in the supernatant were inactivated by adding formaldehyde to the final concentration of 0.8% and then incubated at 4° C. overnight. The formaldehyde treatment also fixes the HIV-1 immunogen, especially the envelope proteins. The inactivated HIV-1 viruses were purified by filtration through 0.45 um filter unit and by high speed centrifugation at 19,000 rpm/min for one hour. The virus pellet was resuspended in PBS at 1/1000 of original volume. The quality and the quantity of the inactivated virus was demonstrated by Western blot analysis using anti-HIV-1 patient serum. The infectivity of the inactivated virus was tested by infecting Jurkat cells as measured by both syncycia formation and the detection of viral antigen released by the cells.

EXAMPLE 2

Construction and Preparation of HIV-1 Pseudovirion

The plasmid HXB/U+R+ contains a replication competent HIV-1 provirus derived from HIVHBX2. In addition to all the essential genes such as gag, pol, env, rev and tat, HXB/U+R+ also expresses vpu, vpr, vif and nef genes. The 5' LTR (HIVHXB2:1 to 675; Ratner et al., Complete Nucleotide Sequences of Functional Clones of the AIDS Virus, *AIDS Res. Hum. Retroviruses*, 3:57–69, 1987) was replaced by the CMV early promoter. The packaging signal in the RNA genome (HIVHXB2:754 to 772) was deleted. The nef gene and the 3' LTR (HIVHBX2:8896–9718) were replaced by the neomycin resistant gene and the polyadenylation signal sequences from the thymidine kinase gene of HSV. The new proviral plasmid, named HXP370, was transfected into COS-7 cells by electroporation. Followed by selection in culture medium containing neomycin, a HIV-1 pseudovirion producer cell line was cloned. The isolation, treatment and characterization of the pseudovirion is the same as that of whole inactivated HIV-1 virus described above.

EXAMPLE 3

Construction and Preparation of Virus Like Particles(VLP)

The DNA fragment containing HIV-1 gag gene derived from HIVHXB provirus plasmid by PCR using 5' primer (HIVHXB2:789–810) and 3' primer (HIVHXB2: 2271–2291). The DNA fragment containing HIV-1 env gene, together with the rev gene that is required for env expression, derived from the provirus plasmid by PCR using 5' primer (HIVHBX2; 5911–5932) and 3' primer (HIVHXB2: 8774–8794) are cloned into the Sindbis vector, respectively (Hahn et al., Infectious Sinbis Virus Transient Expression Vectors for Studying Antigen Processing and Presentation, PNAS, 89:2679–2683, 1992). HIV virus like particles (VLP) containing gag55 (Gheysen et al., Assembly and Release of HIV-1 Precursor Pr55gag Virus Like Particles from Recombinant Baculovirus-Infected Insect Cells, *Cell*, 59:103–112, 1989), gp120 and gp41 can be produced by the Sindbis virus expression system. The preparation and the formaldehyde treatment of the VLP are the same as that of whole HIV-1 virus described above.

EXAMPLE 4

Construction and Preparation of Oligomer HIVgp160

The amino acid sequence of HIV-1 envelope protein is modified at the protese cleavage site of gp120 and gp41 by site specific mutagenesis (HIVHXB: 7773–7785; AAAA-GAGCAGTG changed to GAAGAACCATTG). The new envelope gene, which expresses unprocessed HIV1gp160 was cloned into Sindbis expression vector. The membrane fraction from cells infected by Sindbis/gp160 virus was collected and the HIV-1 envelope protein was isolated and purified by a sepharose-protein G column conjugated with a monoclonal anti-HIVgp120 antibody.

EXAMPLE 5

A *Rhesus Macaque* Primate Model Demonstrating Infectivity with a Simian-Human Immunodeficiency Virus The present invention also provides a molecular hybrid of SIV-1 and HIV-1, simian-human immunodeficiency virus (SHIV), referred herein as SHIV-HXB. This was engineered by replacing the env, tat and rev genes of SIVmac239 with their HIV-1-HXB counterparts. The SHIV-HXB construct also expresses the HIV-1 vpu gene that is absent in all known SIV genomes. This hybrid virus combines SIV's replicative ability in macaque monkeys together with the antigenicity of the HIV envelope protein. SHIV replicates efficiently in macaques cynomolgus with a detectable viremia that lasts about three months. All SHIV infected monkeys have antibodies against HIV-1 envelope glycoprotein as well as the SIV-1 gag proteins (Li et al, *JAIDS*, 5:639–646, 1992). These features indicate that SHIV infection of macaques provides a valid animal model for assessing the efficacy of HIV-1 prophylactics.

*Rhesus macaques* (*Macaca mulata*) are more available than cynomologous macaques and a great deal of data has already accrued from its use in human vaccine and drug studies. To develop this animal model, live SHIV-HXB virus was prepared from infected simian peripheral blood mononuclear cells (PBMC) in large scale. The infectivity of this virus stock was determined by tissue culture infection dose ($TCID_{50}$) titration.

SHIV-HXB replicates efficiently in rhesus monkeys as measured by virus isolation from the peripheral blood of the animals following injection, as shown in Table 1.

TABLE 1

|  | MM421 CD4 Count | MM421 Virus Isolation | MM337 CD4 Count | MM337 Virus Isolation |
|---|---|---|---|---|
| Week 0 | 1,860 | − | 396 | − |
| Week 3 | 1,277 | + | 637 | + |
| Week 5 | 819 | + | 485 | + |
| Week 10 | 2,176 | + | 547 | + |
| Week 15 | 1,802 | − | 837 | − |
| Week 19 | 1,320 | + | 936 | + |
| Week 22 | 3,374 | − | 1,411 | − |
| Week 26 | 2,892 | + | 1,137 | + |
| Week 30 | 2,127 | − | 1,083 | + |
| Week 35 | 2,085 | + | 1,133 | − |
| Week 40 | 2,264 | − | 946 | − |
| Week 43 | 2,911 | − | 816 | − |
| Week 56 | 3,542 | + | 1,357 | + |

However, there was no detectable effect on CD4 cell counts. This agrees with previously published data showing that the peripheral blood of macaques cynomologous were permissive for SHIV replication but without significant effect on the number of the CD4 positive T cells of the infected animals.

In another experiment, two pigtail macaques (*Macaca nemenstrina*) were inoculated with the SHIV-HXB construct by intravenous injection. The two pigtail monkeys Mn134 and Mn135 became virus infected but the CD4 positive T cell counts remained normal, as shown in Table 2.

TABLE 2

|  | MN134 CD4 Count | MN134 Virus Isolation | MN135 CD4 Count | MN135 Virus Isolation |
|---|---|---|---|---|
| Week 0 | 1,787 | − | 1,349 | − |
| Week 2 | 1,115 | + | 1,081 | + |
| Week 4 | 1,729 | + | 1,928 | − |
| Week 6 | 1,329 | + | 2,284 | − |
| Week 10 | 940 | − | 2,171 | + |
| Week 14 | 1,946 | − | 3,121 | − |
| Week 18 | 1,414 | − | 1,852 | − |
| Week 25 | 2,060 | + | 1,799 | − |
| Week 35 | 2,340 | − | 1,882 | − |
| Week 40 | 1,884 | + | 1,082 | − |

None of the four animals in Tables 1 and 2 developed signs of any AIDS-like disease during the period of 60 weeks observation. These data indicate that *rhesus macaques* are useful as an animal model for exploring SHIV infection.

EXAMPLE 6

Determination of SHIV-HXB Doses Establishing Replication in *Rhesus Macaques*

The minimum amount of virus required for establishing productive replication in rhesus monkeys was determined by intravenous injection of four monkeys with 4000, 400, 40 or 4 $TCID_{50}$ units. The animals became infected following the injection as shown in Table 3.

TABLE 3

|  | MmL3 4600 TCID50 | MmL28 460 TCID50 | MmL9 4600 TCID50 | MmJO28 4 TCID50 |
|---|---|---|---|---|
| Week 2 | 460 | 51 | 910 | 100 |
| Week 3 | 4,100 | 8,300 | 37,000 | 1,400 |
| Week 4 | 37,000 | 2,700 | 37,000 | 8,300 |
| Week 6 | 280,000 | 74,000 | 670,000 | 280,000 |
| Week 8 | 110,000 | 110,000 | 670,000 | 330,000 |

The level of virus load in the peripheral blood of the animals was independent of the size of virus inoculum.

In the experiment reported here, four rhesus monkeys. were intravenously injected with 4, 0.4, 0.04 or 0.004 $TCID_{50}$ units. Only the animal inoculated with 4 $TCID_{50}$ became infected, as shown in Table 4.

TABLE 4

|  | MM8A2 4 TCID50 | MMS-88 0.4 TCID50 | MM8B7 0.04 TCID50 | MME363 0.004 TCID50 |
|---|---|---|---|---|
| Week 2 | 6 | ND | ND | ND |
| Week 3 | 460 | ND | ND | ND |
| Week 4 | 910 | ND | ND | ND |
| Week 6 | 25,000 | ND | ND | ND |
| Week 8 | 8,200 | ND | ND | ND |

On the basis of this data, an intravenous injection dose containing 24 $TCID_{50}$ should have 99% probability to infect a rhesus monkey. The same calculation method also predicts that the injection of 5.6 $TCID_{50}$ of this virus would have a 90% infection probability.

EXAMPLE 7

Protection of *Rhesus Macaques* Immunized with Inactivated HIV and Polyphosphazeneto SHIV-HXB A demonstration of the utility of SHIV-HXB in testing the efficacy of HIV-1 vaccine candidates was initiated by the immunization of four rhesus monkeys. The animals were immunized intramuscularly with the following 1 ml formulations in Table 5.

TABLE 5

| Animal | Antigen | Adjuvant |
|---|---|---|
| Mm91069 | HIV-1 gp120 (100 µg) | PCPP (100 µg) |
| Mm91080 | inact. HIV-1 (100 µg) |  |
| Mm91083 | inact. HIV-1 (100 µg) | PCPP (100 µg) |
| Mm91084 | inact. HIV-1 (100 µg) | PCPP (100 µg) |

These four rhesus monkeys and two additional rhesus monkeys Mm421 and Mm337 were intravenously injected with 10,000 $TCID_{50}$ unit of SHIV-HXB.

All the infected animals in Table 1 had serum antibodies against both HIV-1 gp120 and SIV antigens. Cell mediated immune responses specific to HIV-1 gp120 were also detectable in the infected animals. All the animals appeared healthy despite the established virus infection.

Figure 2:
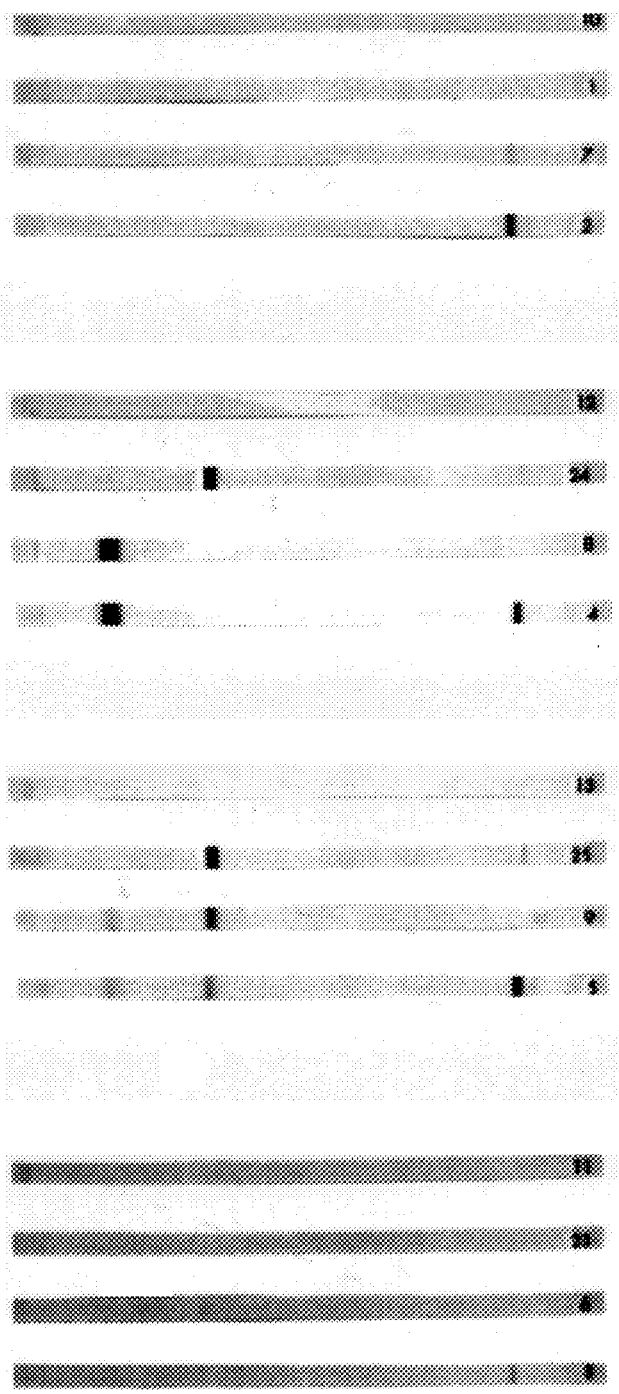
FIG. 2 is a photograph of strips on which a Western analysis was performed that shows the presence of antibodies against HIV-1 gag proteins in the two animals that were inoculated with inactivated HIV-1 virus and polydicarboxylatophenoxy phosphazene (PCPP) as described in Example 1.

All four animals had detectable serum antibodies against HIV-1 gp120 by week 5 after the first immunization (FIG. 1). By week 43, anti-gp120 antibody level had fallen below the level of detection. All four animals received a secondary immunization at week 43 with 100 μg recombinant HIV-1 gp120 plus PCPP. The boost significantly increased the level of all animals' serum anti-gp120 antibodies. The highest titers were seen in animals immunized with inactivated HIV virus plus PCPP. The antibody response in the vaccines was confirmed by Western analysis using a commercial HIV-1 diagnostic kit. As shown in FIG. 2, the two animals that received inactivated virus plus PCPP developed antibodies against HIV-1 gag proteins that were detectable at week 5 and persisted until week 43. All four animals developed comparable anti-gp120 antibodies after the second immunization.

Figure 3:
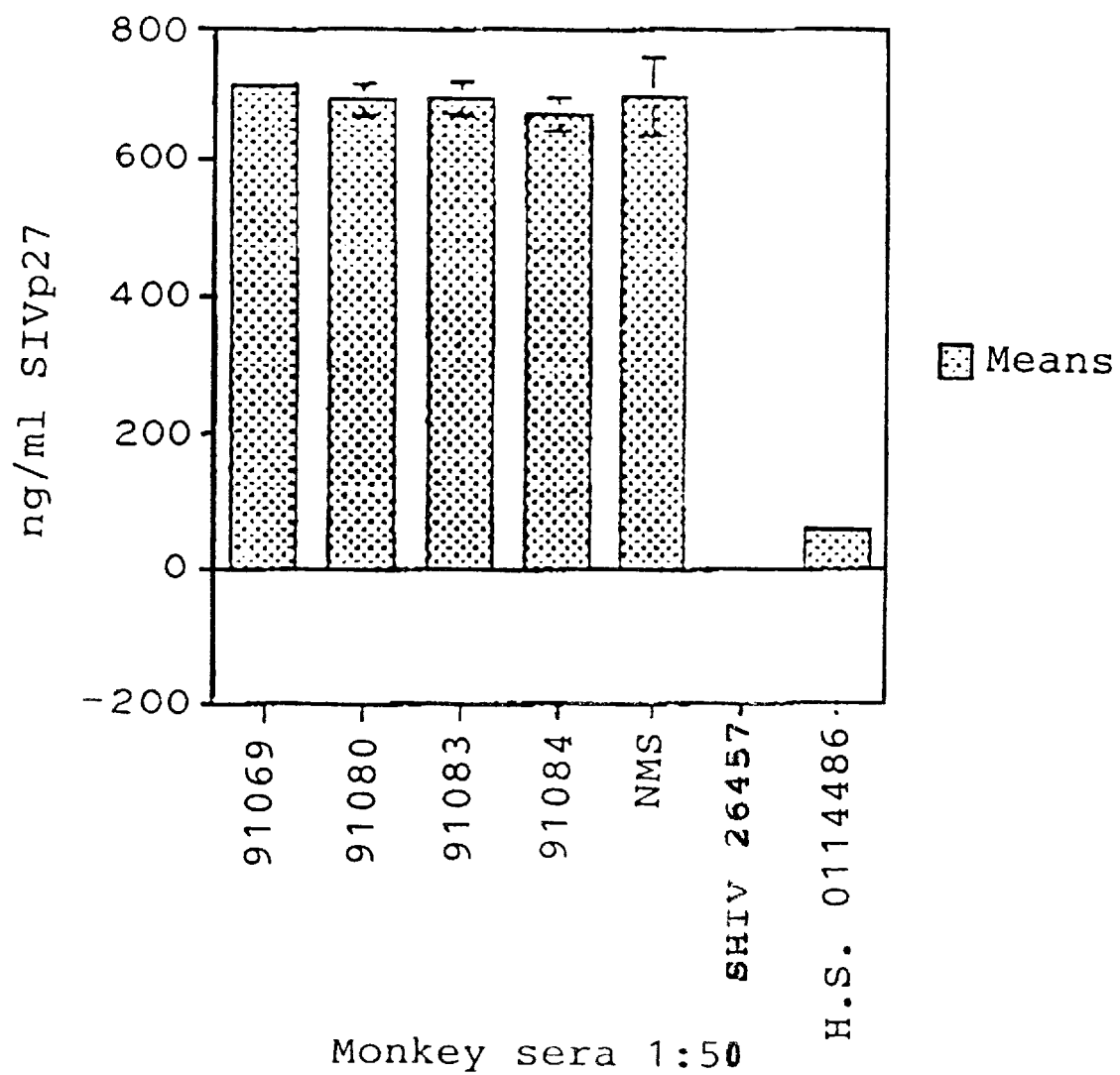
FIG. 3 shows that serum or plasma samples from all four (4) animals in Example 1 showed no detectable neutralizing activity against HIV-1 infection at a dilution factor of 1:50.
Figure 4:
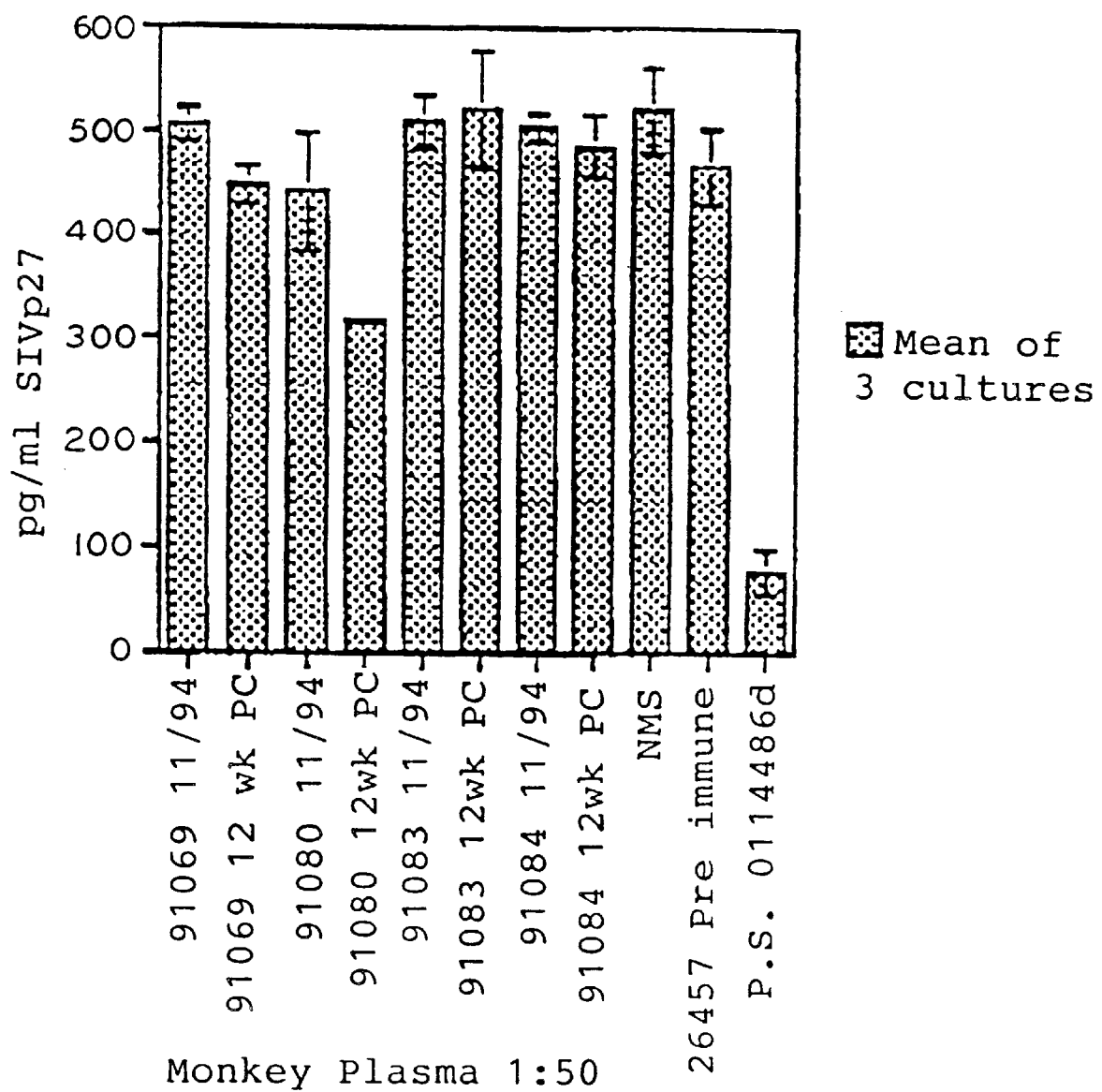
FIG. 4 shows that none of the animals tested as described in Example 1 had detectable HIV-1 neutralizing activity in their plasma at the time of the SHIV challenge.

Even though all the animals developed strong antibody responses against HIV-1 gp120, none of their sera or plasma samples contains detectable neutralizing activity against SHIV infection at a dilution factor of 1:50 (FIG. 3). Furthermore, none of the animals had detectable neutralizing activity in their plasma at the time of the SHIV challenge (FIG. 4).

Figure 6:
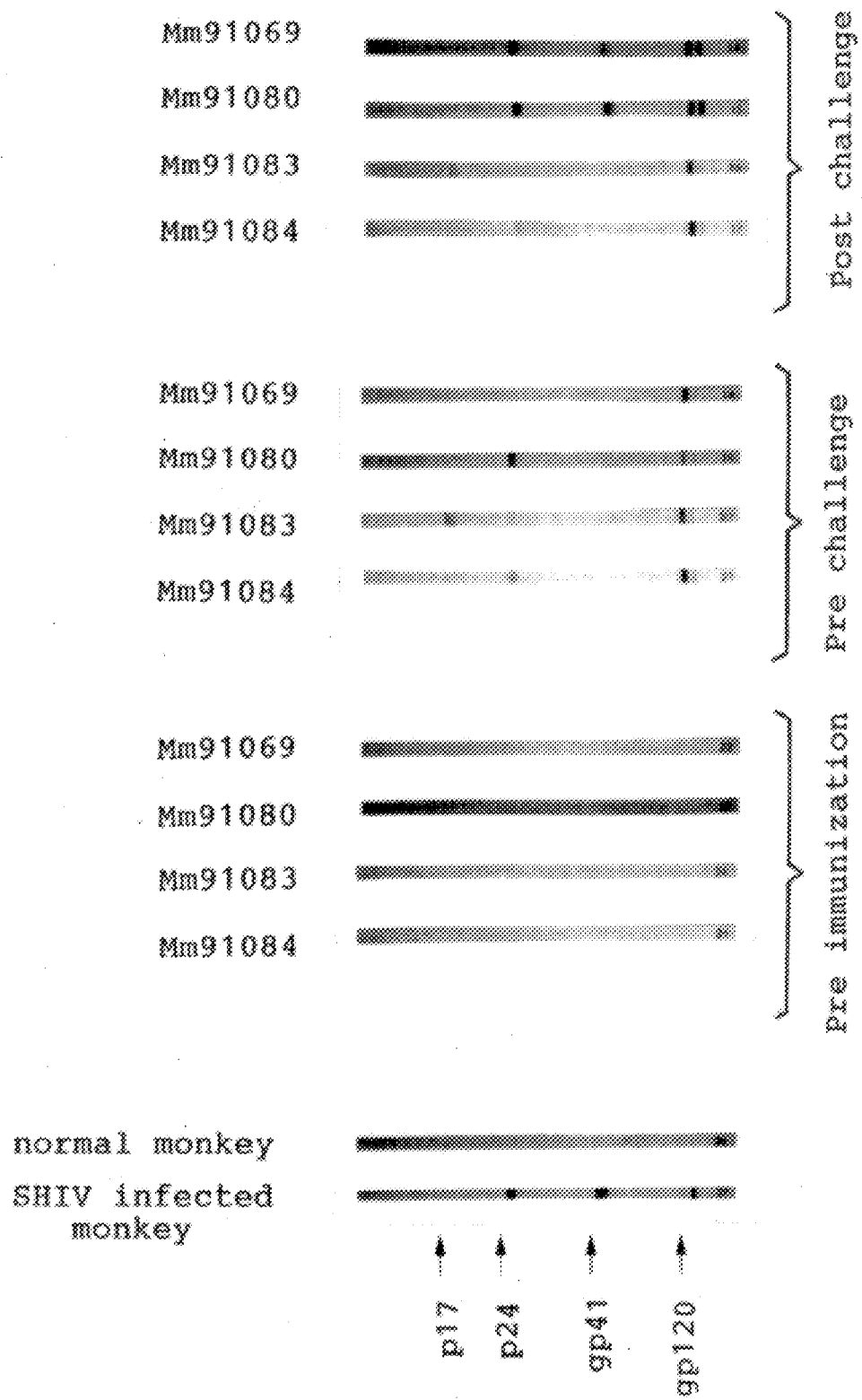
FIG. 6 shows the results of a Western blot analysis of serum samples from animals challenged with SHIV as described in Example 1 comparing the sera as tested before and after the challenge. The two unprotected animals had been immunized with either recombinant HIV-1 gp120 plus PCPP or inactivated HIV alone, whereas the two protected animals were both immunized with inactivated HIV-1 plus PCPP.

A third immunization was administrated to all the animals with the same formulation as in the second immunization at week 73. Two weeks later (week 75), all the vaccines were challenged by intravenous injection of 24 TCID$_{50}$ units of SHIV-HBX, which is calculated to have 99% probability of establishing infection. Blood samples were collected from the animals at three weeks intervals after the SHIV challenge and analyzed for SHIV replication by peripheral blood co-culture with human T cells (FIG. 5) Mm91069 became infected in the first three weeks after SHIV injection. Mm91080 became infected between week 3 and week 6 after injection of SHIV challenge virus. The other two animals, Mm91083 and Mm91084, remained virus isolation negative until the end of the experiment (week 14 post challenge). A Western blot analysis of serum samples from the challenged animals compared the sera from the animals before and after the SHIV challenge (FIG. 6). The protected animals, Mm91083 and Mm91084, show no detectable anti-SHIV antibodies whereas the unprotected animals, Mm91069 and Mm91080, sero-converted to SHIV antigens. Since the four animals differed only in the nature of the antigen used in the primary immunization, it is significant that the two unprotected animals were immunized with either recombinant HIV-1 gp120 plus PCPP (Mm91069) or inactivated HIV only (Mm91080) whereas the two protected animals were both immunized with inactivated HIV plus PCPP (Mm91083 and Mm91084).

The studies presented demonstrate the utility of the SHIV animal model in efficacy studies of HIV prophylactics.

Additional SHIV chimeric viruses have been constructed utilizing envelope genes from HIV-ELi, HIV-MN, and HIV-89.6. Each virus stock was propagated in rhesus PBMCs and their TCID$_{50}$ determined. Both SHIV-MN and SHIV-89.6 grow productively in rhesus monkeys and more over SHIV-89.6 demonstrates efficient non-traumatic vaginal mucosal penetrance and infection(Y. Lu and C. Miller, unpublished observation). A range of SHIV constructs titered and characterized for growth in non-human primates permits the evaluation of the breath of immune protection afforded different antigen formulation against challenge with different isolates and by different routes of infection.

This study shows that it is possible to stimulate protective immunity in rhesus monkeys against SHIV infection by using inactivated HIV-1 plus a polyphosphazene adjuvant.

What is claimed is:

1. An immunogenic composition comprising
   (a) a member selected from the group consisting of replication incompetent HIV-1, HIV-1 pseudovirus, HIV-1 VLP and oligomeric gp120; and
   (b) a water soluble polyphosphazene polyelectrolyte, wherein (a) and (b) are present in an immunogenic effective amount.

2. The polyphosphazene polyelectrolyte of claim 1 wherein the polyphosphazene contains charged side groups, either in the form of an acid or base that is in equilibrium with its counter ion, or in the form of an ionic salt thereof.

3. The polyphosphazene polyelectrolyte of claim 1 having the formula $$\left(\begin{array}{c} R \\ | \\ P=N \\ | \\ R \end{array}\right)_n$$

wherein each R is independently selected from the group consisting of aliphatic, aryl, aralkyl, alkaryl, carboxylic acid, heteroaromatic, carbohydrates, heteroalkyl, halogen, (aliphatic)amino-, heteroaralkyl, di(aliphatic)amino-, arylamino-, diarylamino-, alkylarylamino-, -oxyaryl, -oxyaliphatic, -oxy(aliphatic)hydroxyl, -oxyalkaryl, -oxyaralkyl, thioaryl, -thioaliphatic, -thioaralkyl, —NHC(O)O—(aryl or aliphatic), —O—((CH$_2$)$_x$O)$_y$—(CH$_2$)$_x$NH$_2$ and —O—((CH$_2$)$_x$O)$_y$—(aryl or aliphatic, wherein x is 1–8, y is an integer of 1 to 20 and n is an integer of at least 4 or more.

4. The polyphosphazene of claim 1 having the formula:

$$\left(\begin{array}{c} A \\ | \\ P=N \\ | \\ B \end{array}\right)_n$$

wherein A and B can vary independently in the polymer, and can be:
   (i) a group that is susceptible to hydrolysis under the conditions of use, including but not limited to chlorine, amino acid, amino acid ester (bound through the amino group), imidazole, glycerol, or glucosyl; or
   (ii) a group that is not susceptible to hydrolysis under the conditions of use, including, but not limited to an aliphatic, aryl, aralkyl, alkaryl, carboxylic acid, heteroaromatic, heteroalkyl, (aliphatic)amino- including alkylamino-, heteroaralkyl, di(aliphatic) aminoincluding dialkylamino-, arylamino-, diarylamino-, alkylarylamino-, -oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy(aliphatic)PO$_3$H, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, or thioaralkyl;
wherein the polymer contains at least one percent or more, preferably 10 percent or more, and more preferably 80 to 90 percent or more, but less than 100%, of repeating units that are not susceptible to hydrolysis under the conditions of use; and
wherein n is an integer of at least 4 or more.

* * * * *